United States Patent
Düzgünes et al.

(10) Patent No.: US 6,245,427 B1
(45) Date of Patent: Jun. 12, 2001

(54) NON-LIGAND POLYPEPTIDE AND LIPOSOME COMPLEXES AS INTRACELLULAR DELIVERY VEHICLES

(76) Inventors: Nejat Düzgünes, 508 Pixie Trail, Mill Valley, CA (US) 94941; Sérgio Simões, Rua Henrique Seco 33 Esq., 3000 Coimbra (PT); Vladimir Slepushkin, 2013 10th St. Ct., Coralville, IA (US) 52241; Maria C. Pedras de Lima, Rua Padre Americo 42, 4 Esq., 3000 Coimbra (PT)

( * ) Notice: Subject to any disclaimer, the term of this patent is extended or adjusted under 35 U.S.C. 154(b) by 0 days.

(21) Appl. No.: 09/111,265

(22) Filed: Jul. 6, 1998

(51) Int. Cl.[7] .............................. B32B 9/02; C12N 15/88; C07K 14/00; C07K 14/765; C07H 21/04

(52) U.S. Cl. ...................... 428/402.2; 435/458; 530/363; 530/350; 536/23.1; 424/9.321

(58) Field of Search .............................. 435/458; 530/363, 530/350; 536/23.1; 428/402.2; 424/9.321

(56) References Cited

U.S. PATENT DOCUMENTS

| | | |
|---|---|---|
| 5,521,291 | 5/1996 | Curiel et al. . |
| 5,547,932 | 8/1996 | Curiel et al. . |

FOREIGN PATENT DOCUMENTS

WO 97/28817    8/1997    (WO) .

OTHER PUBLICATIONS

Simoes et al. Human serum albumin enhances DNA transfection by lipoplexes and confers resistance to inhibition by serum. Biochimica Biophysica Acta vol. 1463 pp. 459–469, 2000.*

Singhal A, Huang L, Gene transfer in mammalian cells using liposomes as carriers, Gene Therapeutics: Methods and Applications of Direct Gene Transfer, In: Wolf JA (ed) Birkhäuser: Boston, pp. 118–142 (1994).

Lee RJ, Huang L, Folate–targeted, anionic liposome–entrapped polylysine–condensed DNA for tumor cell–specific gene transfer, J Biol Chem, 271:8481–8487 (1996).

Treco DA, Selden RF, Non–viral gene therapy, Molecular Medicine Today, 1:314–321 (1995).

Hug P, Sleight RG, Liposomes for the transformation of eukaryotic cells, Biochim Biophys Acta, 1097: 1–17 (1991).

Lasic DD, Templeton NS, Liposomes in gene therapy, Adv Drug Deliv Rev, 20: 221–266 (1996).

Liu Y et al, Cationic liposome–mediated intravenous gene delivery, J Biol Chem, 270:24864–24870 (1995).

Thierry AR et al, Systemic gene therapy: bio–distribution and long–term expression of a transgene in mice, Proc Natl Acad Sci USA, 92:9742–9746 (1995).

Takehara T et al, Expression of the hepatitis C virus genome in rat liver after cationic liposome–mediated in vivo gene transfer, Hepatology, 21: 746–751 (1995).

Felgner PL et al Editorial: Nomenclature for synthetic gene delivery systems, Hum Gene Therapy, 8: 511–512 (1997).

Cheng PW, Receptor ligand–facilitated gene transfer: Enhancement of liposome–mediated gene transfer and expression by transferrin, Hum Gene Therapy, 7: 275–282 (1996).

Simões S, Slepushkin V, R. Gaspar, Pedroso de Lima MC, Düzgünes N, Gene delivery by negatively charged ternary complexes of DNA, cationic liposomes and transferrin or fusigenic peptides, Gene Therapy, 5: 955–964 (1998).

Konopka K, Harrison GS, Felgner P, Düzgünes N, Cationic liposome–mediated expression of HIV–regulated luciferase and diphtheria toxin A genes in HeLa cells infected with or expressing HIV, Biochim Biophys Acta, 1356: 185–197 (1997).

Remy J–S et al, Targeted gene transfer into hepatoma cells with lipopolyamine–condensed DNA particles presenting galactose ligands: a stage towards artificial viruses, Proc Natl Acad Sci USA, 92: 1744–1748 (1995).

Zhu N et al, Systemic gene expression after intravenous DNA delivery into adult mice, Science, 261: 209–211 (1993).

Reed RG Burrington CM, The albumin receptor effect may be due to a surface–induced conformational change in albumin, J Biol Chem, 264: 9867–9872 (1989).

Allen TM Moase EH, Therapeutic opportunities for targeted liposomal drug delivery, Adv Drug Deliv Rev, 21: 117–133 (1996).

Hansen CB et al Attachment of antibodies to sterically stabilized liposomes: evaluation, comparison and optimization of coupling procedures, Biochim Biophys Acta, 1239: 133–144 (1995).

Kaneda Y et al, Increased expression of DNA cointroduced with nuclear protein in adult rat liver, Science, 243: 375–378 (1989).

(List continued on next page.)

*Primary Examiner*—John S. Brusca
(74) *Attorney, Agent, or Firm*—David Dolberg, Esq.

(57) ABSTRACT

The present invention discloses compositions and methods of using intracellular delivery vehicles for delivery and transfection of DNA, RNA, polypeptides, genes, proteins, drugs and biologically active agents into cells in vitro and in vivo. The vehicle comprises a mixture of a liposome and a polypeptide lacking specificity for cellular receptors. In another embodiment, a method for intracellular delivery of biologically active agents comprising combining a non-receptor-binding protein and a liposome, incubating the mixture for a period of time, adding the biologically active agent, incubating again, and finally, introducing the resulting mixture to the cell. Preferably, the liposome is a cationic liposome. The charge ratio of cationic liposome to DNA can effectively be varied from 2:1 to 1:2. Preferably, the non-receptor-binding protein is the serum albumin of the animal source of the cell to be transfected. This inention is an improvement over, and offers several advantages compared to, previously disclosed cationic liposomal delivery vehicles which utilize receptor ligands.

41 Claims, 9 Drawing Sheets

OTHER PUBLICATIONS

Kaneda Y, Introduction and expression of the human insulin gene in adult rat liver, J Biol Chem, 264: 12126–12129 (1989).

Konopka K, Pretzer E, Felgner PL, Düzgünes N, Human immunodeficiency virus type–1 (HIV) infection increases the sensitivity of macrophages and THP–1 cells to cytotoxicity by cationic liposomes, Biochim Biophys Acta, 1312: 186–196 (1996).

Ciccarone V Hawley–Nelson P Jessee J, Cationic liposome–mediated transfection: effect of serum on expression and efficiency, Focus, 15: 80–83 (1993).

Li S, Huang L Lipidic supramolecular assemblies for gene transfer, J Liposome Res, 6: 589–608 (1996).

Gershon H et al., Mode of formation and structural features of DNA–cationic liposome complexes used for transfection, Biochemistry, 32: 7143–7151 (1993).

Legendre J–Y Szoka FCJr, Cyclic amphipathic peptide–DNA complexes mediated high–efficiency transfection, of mammalian cells, Proc Natl Acad Sci USA, 90:893–897 (1993).

Heslop HE et al, Long–term restoration of immunity against Epstein–Barr virus infection by adoptive transfer of gene–modified virus–specific T lymphocytes, Nature Medicine, 2: 551–555 (1996).

Blaese RM et al T lymphocyte–directed gene therapy for ADA–SCID: Initial trial results after 4 years, Science, 270: 475–480 (1995).

Yu M, Poeschla E, Wong–Staal F, Progress towards gene therapy for HIV infection, Gene Therapy, 1:13–26 (1994).

Konopka K Düzgünes N Rossi J Lee NK, Receptor ligand–facilitated cationic liposome delivery of anti–HIV–1 Rev–binding aptamer and ribozyme DNAs, J Drug Targeting, 5: 247–259 (1998).

Harrison GS et al, Inhibition of human immunodeficiency virus–1 production resulting from transduction with a retrovirus containing an HIV–regulated diphtheria toxin A chain gene, Human Gene Therapy 3: 461–469 (1992).

Subbarao NK et al, pH–dependent bilayer destabilization by an amphipathic peptide, Biochemistry, 26: 2964–2972 (1987).

Parente RA et al, pH–dependent fusion of phosphatidylycholine small vesicles, J Biol. Chem, 263: 4724–4730 (1988).

Lasic et al. Novel applications of liposomes. Trends in Biotechnology vol. 16 pp. 307–321, 1998.*

Kamata et al. Amphiphilic peptides enhance the efficiency of liposome–mediated DNA transfection. Nucleic Acids Res. vol. 22 pp. 536–537, 1994.*

Malone et al. Cationic liposome–mediated RNA transfection. Proc. Natl. Acad. Sci. USA vol. 86 pp. 6077–6081, 1989.*

Mack et al. Polylysine enhances cationic liposome–mediated transfection of the hepatoblastoma cell line Hep G2. Biotechnol. Appl. Biochem. vol. 23 pp. 217–220, 1996.*

Gao et al. Potenitation of cationic liposome–mediated gene delivery by polycations. Biochemistry vol. 35 pp. 1027–1036, 1996.*

Orkin et al. report and recommendations of the panel to assess the NIH investment in research on gene therapy. pp. 1–41, 1995.*

* cited by examiner

NON-LIGAND POLYPEPTIDE AND LIPOSOME COMPLEXES AS INTRACELLULAR DELIVERY VEHICLES

FIELD OF THE INVENTION

This invention relates generally to intracellular substance delivery the intracellular delivery of biologic molecules. More specifically, it relates to the use of liposomal complexes for intracellular delivery of biologically active agents.

BACKGROUND OF THE INVENTION

One of the major problems of gene therapy is the effective delivery of the therapeutic agent into target cells in vitro or in vivo. Although viral vectors have certain advantages, including high levels of transfection, or efficient and stable integration of foreign DNA into a wide range of host genomes, they suffer from several problems including immunogenicity, toxicity, difficulty of large-scale production, size limit of the exogenous DNA, random integration into the host genome, and the risks of inducing tumorigenic mutations and/or generating active viral particles through recombination (Singhal, A. and Huang, L., (1994) In: Wolf, J. A.(ed), *Gene Therapeutics: Methods and Applications of Direct Gene Transfer*. Birkhauser: Boston, pp118–142: Lee, R. J., and L. Huang, (1996) *J. Biol. Chem.* 271:8481–8487). These limitations of viral vectors have prompted investigators to try to improve methods of non-viral gene delivery. (Treco, D. A. and R. F. Selden, (1995) *Mol. Med. Today* 1:314–321).

Cationic liposomes have been used extensively for in vitro and in vivo gene delivery, and constitute a viable alternative to viral gene delivery vehicles. (Singhal A., and L. Huang, supra; Hug P and R. G. Sleight, (1991) *Biochim Biophys Acta* 1097: 1–17: Lasic D. D. and N. S. Templeton, (1996) *Adv. Drug Deliv. Rev.* 20: 221–266). Using this delivery system, relatively stable expression has been achieved in a number of tissues. (Liu, Y., et al., (1995) *J Biol Chem* 270: 24864–24870: Thierry, A. R., et al., (1995) *Proc Natl Acad Sci USA* 92: 9742–9746: Takehara, T., et al., (1995) *Hepatology* 21:46–751.)

The efficiency of cationic liposome transfection was improved through the use of two different approaches. The first approach was based on the promotion of cellular internalization of the cationic liposome-DNA complexes through receptor-mediated endocytosis. For this purpose iron-saturated human transferrin, and other receptor-mediated ligands, were associated with the lipid-DNA complexes, referred to herein as "lipoplexes" (Felgner,et al., (1997) *Hum. Gene Ther.* 8: 511–512) at different (+/−) charge ratios. Transferrin is a useful ligand that binds to a cell-surface receptor expressed by most proliferating cells, with particularly high expression on erythroblasts and tumor cells (Wagner et al., (1994) *Adv. Drug. Del. Rev.* 14:113–136). Another report indicated that associating transferrin with cationic liposomes also enhanced transfection of HeLa cells (Cheng, P. W. (1996) *Hum. Gene Ther.* 7:275–282). The use of transferrin as a receptor-ligand in lipoplex-mediated transfections was also disclosed by Cheng, P. W. in PCT publication WO 97/28817, incorporated herein by reference is referred to hereinafter as "Cheng (1997)".

The second approach was based on the association of endosome disrupting agents to the lipoplexes with the purpose of facilitating the cytoplasmic release of DNA from endosomes, thus preventing its lysosomal degradation and therefore enhancing transfection. Two different synthetic fusogenic peptides, "GALA" and the influenza virus hemagglutinin HA2 N-terminal peptide (hereinafter, "HA-2"), both low pH-activated rrtmbrane-active peptides, were used for that purpose (Simoes, S. et al.(1998) *Gene Ther.*, in press).

The use of receptor-specific ligands as a targeting protein in liposomal delivery vehicles in vitro and in vivo presents several problems. Receptor-specific ligands are relatively rare molecules and incur considerable expense in isolating and collecting an adequate supply. Receptor-ligands are invariably potent effectors of biological response. Use of such molecules in lipoplexes increase their concentration in the cellular milieu and therefore pose a potentially serious threat of adverse or unwanted side-effects. Finally, studies have shown that high concentrations of blood serum can inhibit the efficiency of ligand-mediated lipoplexes, thereby raising serious questions as to their utility in an in vivo environment. (Cheng (1997).

SUMMARY OF THE INVENTION

This invention describes unique liposomal complexes for the intracellular delivery of particular agents or molecules such as DNA, RNA or proteins. This invention also describes methods for the use of these complexes for intracellular delivery. A unique feature of this invention is that it utilizes polypeptides that lack cell-receptor specificity (non-ligands, also referred to as non-receptor-binding polypeptides) combined with cationic liposomes as a delivery vehicle. Molecules desirable for intracellular delivery include, but are not limited to DNA, polydeoxyribonucleotides, RNA, polyribonucleotides, proteins, peptides, polypeptides and the like.

It is an object of this invention to provide carrier compositions for intracellular delivery of a biologic molecule or agent.

It is an object of this invention to provide carriers that do not include viral components.

It is an object of this invention to provide carriers that do not utilize receptor-ligands or receptor-mediated transport molecules.

It is an object of this invention to provide carriers that comprise liposomes and serum proteins that bind to cells non-specifically.

It is an object of this invention to utilize vehicle components that are abundant, inexpensive and easy to isolate in large quantity.

It is an object of this invention to provide a vehicle whose components are not likely to cause an undesirable biological reaction.

It is an object of this invention to provide a vehicle that is effective in the presence of high concentrations of blood serum.

It is an object of this invention to provide methods of using carrier cdmpositions to effect intracellular delivery of particular molecules.

In accordance with the above objects and other described herein, the carrier composition for intracellular delivery of a biologically active molecule of the present invention comprises a mixture of a cationic lipid and a non-receptor-binding protein.

In another embodiment of the invention the cationic lipid is combined with a neutral lipid forming a cationic liposome thereby.

In another embodiment, the carrier composition comprises a cationic lipid and serum albumin of human or non-human origin.

In another embodiment, the carrier composition comprises a cationic lipid, a protein that lacks receptor specificity (a non-receptor-binding protein) and a biologically active molecule.

In further accordance with the above objects and others described herein, the method for intracellular delivery of a biologically active agent to a target cell comprises:

a) combining a non-receptor-binding polypeptide and a cationic lipid to form a first mixture such that said polypeptide and cationic lipid become associated;

b) adding to said first mixture said biologically active agent to form a second mixture such that said agent becomes associated with said cationic lipid; and, c) introducing said second mixture to said cell.

In another embodiment of the method, the non-receptor-binding polypeptide is a protein. In a preferred embodiment, the protein is a serum albumin, most preferably, the serum albumin of the animal source of the target cell to be inoculated.

In another embodiment of the method, the cationic lipid is combined with a neutral lipid forming a cationic liposome thereby.

DESCRIPTION OF THE DRAWINGS

For a further understanding of the objects and advantages of the present invention, reference should be made to the accompanying drawings taken in conjunction with the detailed description, wherein.

DETAILED DESCRIPTION OF THE INVENTION

Figure 1:
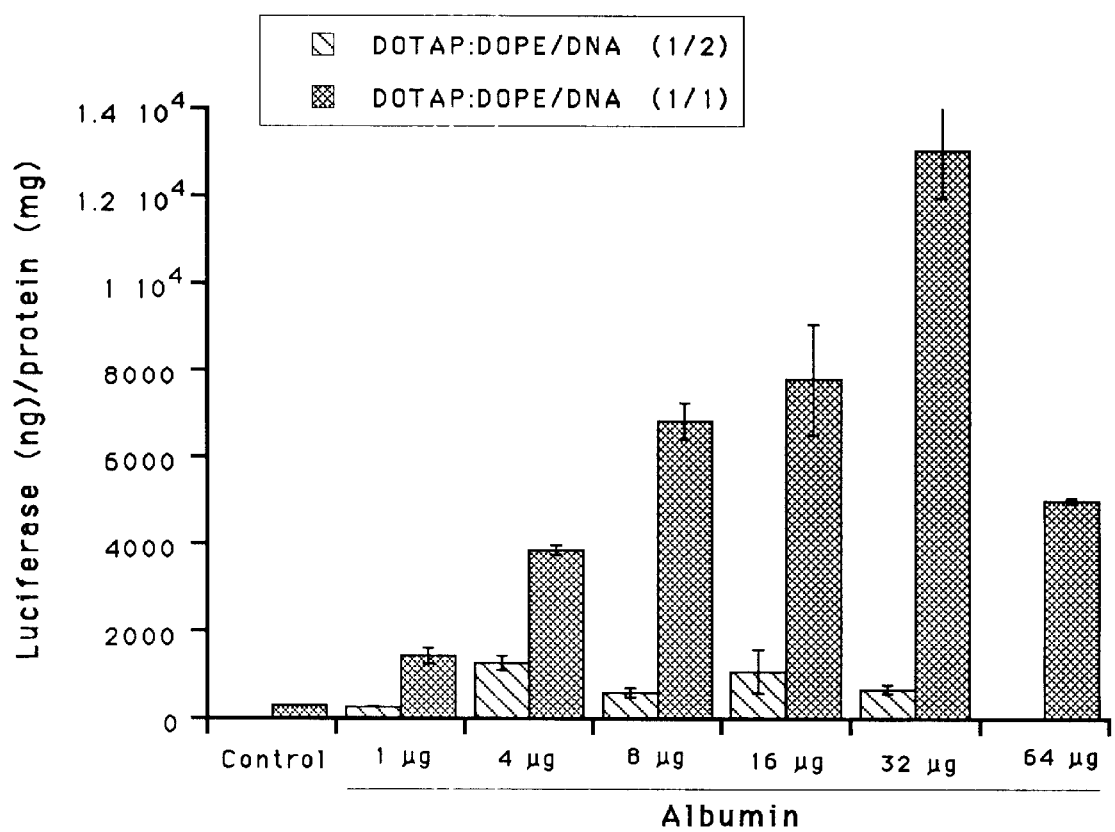
FIG. 1 shows a comparison of the effects of varying concentrations of human serum albumin (HSA) in lipoplexes on luciferase gene expression in COS-7 cells.

The successful application of gene therapy strategies is strongly dependent on the development of systems capable of carrying and delivering transgenes to the desired target cells. Potential problems with the use of viral vectors, including their immunogenicity and pathogenicity, necessitate the development of non-viral vectors for gene delivery.

The efficiency of gene transfer mediated by lipid-based gene delivery systems, namely cationic liposomes, is limited by their ability to condense DNA in order to ensure its protection against nuclease degradation and its internalization into cells. Several barriers, including the cytoplasmic, endosomal and nuclear membranes, have to be overcome for effective intracellular delivery and expression of transgenes into the desired cells.

In an attempt to circumvent the limitations associated with the low levels of transfection usually achieved using gene delivery mediated by lipoplexes (lipid/DNA complexes), receptor-mediated targeting ligands (e.g., transferrin) have been used as a component of the lipoplex to promote their internalization, presumably by receptor-mediated endocytosis (Cheng, (1997), supra; Simoes, S., et al., (1998), supra). This strategy has been effective in enhancing transfection in a large variety of cells, including epithelial and lymphoid cell lines as well as human macrophages, especially with the use of optimized lipid/DNA (+/−) charge ratios (Simoes, S. et al., (1998), submitted for publication). Nevertheless, while Cheng ((1997), supra), discloses receptor ligands as a lipoplex component, the actual mechanisms by which the resulting complexes promoted gene transfer and enhanced transfection were not completely understood.

Although liposomal vectors, including those utilizing receptor ligands such as transferrin, share several advantages including lack of immunogenicity, safety, ability to package large DNA molecules, and ease of preparation (Singhal, A. and L. Huang (1994), supra; Lee, R. J., and L. Huang, (1996), supra), they have a limited efficiency of delivery and gene expression, toxicity at higher concentrations (Konopka, et al., (1997) *Biochim Biophys Acta.* 1356:185–197), potentially adverse interactions with biological milieu rich in negatively charged macromolecules (Lee, R. J. and L. J. Huang, (1996), supra; Remy, J-S., et al., (1995) *Proc. Natl. Acad. Sci. USA* 92: 1744–1748), side effects resulting from the abnormally high concentrations of the ligand molecule in proximity to and within the cell, the high cost in obtaining sufficiently pure quantities of ligand, and inability to reach tissues beyond the vasculature unless directly injected into the tissue. In the later regard, genes delivered in vivo via cationic liposomes are expressed primarily in cells of the vascular compartment (Zhu N, et al., (1993) *Science* 261: 209–211: Liu Y et al., (1995) *J. Biol. Chem.* 270: 24864–24870), although transgene expression has also been noted in deep tissues (Zhu, et al., (1993), supra). Furthermore, cationic lipoplexes may be coated in vivo with serum proteins such as lipoproteins, complement and immunoglobulins, or bind non-specifically to cells such as erythrocytes, lymphocytes and endothelial cells, as well as to extracellular matrix proteins. This may limit the ability of the complexes to reach target tissues and cells (Singhal et al., (1994), Hug, P. and Sleight, R. G., (1991) *Biochim. Biophys. Acta* 1097: 1–17: and Remy, J. S., et al., *Proc. Natl. Acad. Sci. USA.* (1995) 92:9742–9746).

The instant invention discloses ternary lipoplex complexes that do not utilize receptor ligands, but use instead polypeptides and proteins that do not have a specific affinity for cell surface receptors and do not show any evidence of ligand-receptor type interactions. In a preferred embodiment, serum albumin, e.g. human serum albumin (hereinafter, "HSA"), is complexed with a cationic liposome to provide a carrier composition for intracellular delivery of a biological molecule or agent (a combination of different biological molecules). Albumin is considered to be the archetype of a protein that lacks a specific cell-surface receptor (Reed, R. G. and C. M. Burrington (1989) *J. Biol. Chem.* 264:9867–9872). This piotein is present in most tissue culture media as well as blood sera. It is readily available, purified, in large quantities. The association of HSA to lipid/DNA complexes may overcome some of the limitations associated with the use of cationic liposomes in gene therapy. Indeed, the ternary complexes of cationic liposomes, DNA, and HSA, not only lead to high levels of transfection, but also have the advantages of being active in the presence of serum and, because HSA is already ubiquitous at high concentrations in tissue culture media as well as in vivo, being non-toxic. Moreover, such negatively charged ternary complexes are likely to alleviate the problems associated with the use of highly positively charged complexes in vivo, such as avid complexation with serum proteins. This is a novel and unexpected improvement over the invention of Cheng (1997, supra).

Generally, the methods of this invention can employ any mono- or polycationic lipid, or any mono- or polycationic lipid and neutral lipid, whether or not the lipid(s) are in a cationic liposome formulation. Cationic lipids, including, but not limited to:

DOTMA (N-[1-(2,3-dioleyloxy)propyl]-N,N,N-trimethyl) ammonium bromide; DDAB (dimethyl dioctadecyl ammonium bromide;

DOSPA (2,3-dioleyloxy-N-[2(sperminecarboxamido)ethyl]-N,N-dimethyl-1-propanaminium trifluoro acetate);

DORI (1,2-dioleoyl-3-dimethyl-hydroxyethyl ammonium bromide);

DORI-ester; DORI-ether;

DMRIE (1,2-dimyristyloxypropanol-3,3-dimethylhydroxymethyl ammonium bromide);

DOTAP (1,2-bis (oleoyloxy)-3-(trimethylammonio) propane); or,

TM-TPS (N,N',N',N''',N'''-tetrapalmitylspermine), and structurally related cationic lipids, are known by those skilled in the art. Compositions for each of these acronyms are also well known in the art.

Other cationic lipids and lipid reagents are commercially available. These include: Eu-Fectin™ reagents (JBL Scientific); Escort™ reagent (Sigma); Lipofectin , Lipofectace™, Lipofectamine™, and Lipofectamine Plus™ (all available from GIBCO-BRL); Fugene 6™; Prefect Lipids™ (Invitrogen); Vectamidine™ (Biotech Tools); Transfast™ Transfection Reagent (Promega); DMRIE-C™ (GIBCO-BRL); Transfectam™ (Promega); Lipo Taxi™ (Stratagene); Gene Transfers™ (WAKO); GS288 Cytofectin™ (Gilead) ethyl phosphatidylcholine (Avanti); and other similar reagents known to those in the art.

Also useful as cationic transfection reagents are branched polymers known as "dendrimers" (e.g. Superfect™ (Qiagen), an activated dendrimer). Such reagents are also useful instead of cationic lipids in the present invention.

Useful cationic liposomes include, but are not limited to, those in which the neutral lipid is DOPE (dioleoylphosphatidylethanolamine), or cholesterol.

Polypeptides and proteins that lack specificity for cell receptors (non-ligands) useful in the instant invention include generally serum albumins or polypeptide fragments of serum albumins—including but not limited to human, bovine, porcine, murine and the like. Other useful polypeptides lacking specificity for cell receptors include, but are not limited to, apotransferrin.

Generally, the constructs of the present invention are made by mixing one or more cationic lipids, or liposomes, with a polypeptide or protein or protein fragment that lacks specificity for cellular receptors (such as a serum albumin), incubating for a period of time, adding the biological agent and incubating again, and then providing the resulting mixture to the target cell. If the target cell is in culture, the mixture can be overlaid upon the cells. If the target cell is in the animal (in vivo), the mixture can be injected into the blood stream or infused in situ into the target tissue.

In another embodiment, the non-ligand polypeptide is covalently attached to an active lipid which is part of, or later incorporated into the liposome. The coupling of polypeptides to an active lipid is know to those skilled in the art (Allen, T. M. and E. H. Morse, *Adv. Drug Deliv. Rev.* (1996) 21:117–133: Hansen, C. B., et al., *Bichim Biophys. Acta* (1995) 1239:133–144).

The methods and constructs of this invention can be employed with any known techniques for enhancing expression of genes transfected into cells. For example, co-introduction of nuclear protein along with DNA in liposomes (Kaneda, Y., et al, (1989) *Science* 243:375–378: Kaneda, Y., et al, (1989) *J. Biol. Chem.* 264(21):12126–12129). Those of ordinary skill in the art will appreciate that all non-receptor-specific proteins, and cationic liposomes other than those specifically exemplified herein can be employed in view of the descriptions and methods provided herein. The constructs of non-receptor-specific proteins and cationic liposomes described herein can readily be adapted based on the disclosures of this invention to introduce not only genes, gene fragments, DNA, poly-deoxyribonucleotides, oligo-deoxyribonucleotides and the like; but also RNA, poly-ribonucleotides, oligo-ribonucleotides, proteins, polypeptides, oligopeptides, drugs and the like (Wagner, E., et al., (1994) *Adv. Drug Del. Rev.* 14, 113–135).

RESULTS

TRANSFECTION ACTIVITY AS A FUNCTION OF THE AMOUNT OF HUMAN SERUM ALBUMIN ASSOCIATED WITH LIPOPLEXES. The limited efficiency of transfection mediated by non-viral vectors, especially when compared to that by viral vectors, is one of the main restrictions to the more frequent use of these systems in gene therapy. In an attempt to optimize the use of lipid-based gene delivery systems, cationic lipids and combined cationic and neutral lipids (cationic liposomes), such as liposomes containing DOTAP:DOPE, complexed with the most abundant serum protein, human serum albumin, and DNA at different cationic lipid/DNA charge ratios were prepared as described in Methods.

The transfection activity obtained with the ternary complexes of cationic liposome-DNA-HSA was dependent on the amounts of HSA used. As shown in FIG. 1, transfection as measured by luciferase gene expression in COS-7 cells in culture is dependent upon the amount of HSA complexed with DOTAP:DOPE liposomes. Cells were rinsed twice with serum-free medium and then covered with 0.3 ml of DME-HG before lipid/DNA complexes were added. The liposomes were complexed, in the presence or absence of different amounts of HSA, with 1 μg of pCMVluc at the indicated theoretical lipid/DNA charge ratios. After an incubation for 4 hours, the medium was replaced with DME-HG containing 10% FBS and the cells were further incubated for 48 hours. The level of gene expression was evaluated as described in Methods. The data are expressed as ng of luciferase per mg of total cell protein (mean±standard deviation obtained from triplicate wells), and are representative of 2 independent experiments.

An enhancement of transfection was observed as the amount of albumin associated with (1/1) DOTAP:DOPE/DNA complexes was increased up to 32 μg. Doubling this amount led to a decrease in the level of luciferase gene expression, indicating that the presence of 32 μg of HSA results in the optimal conditions for transfection. Ternary complexes of HSA with DOTAP:DOPE/DNA at a (1/2) (+/−) charge ratio also enhanced transfection of the plain lipoplexes, but to much lower levels compared to that obtained with the (1/1) charge ratio.

Figure 2:
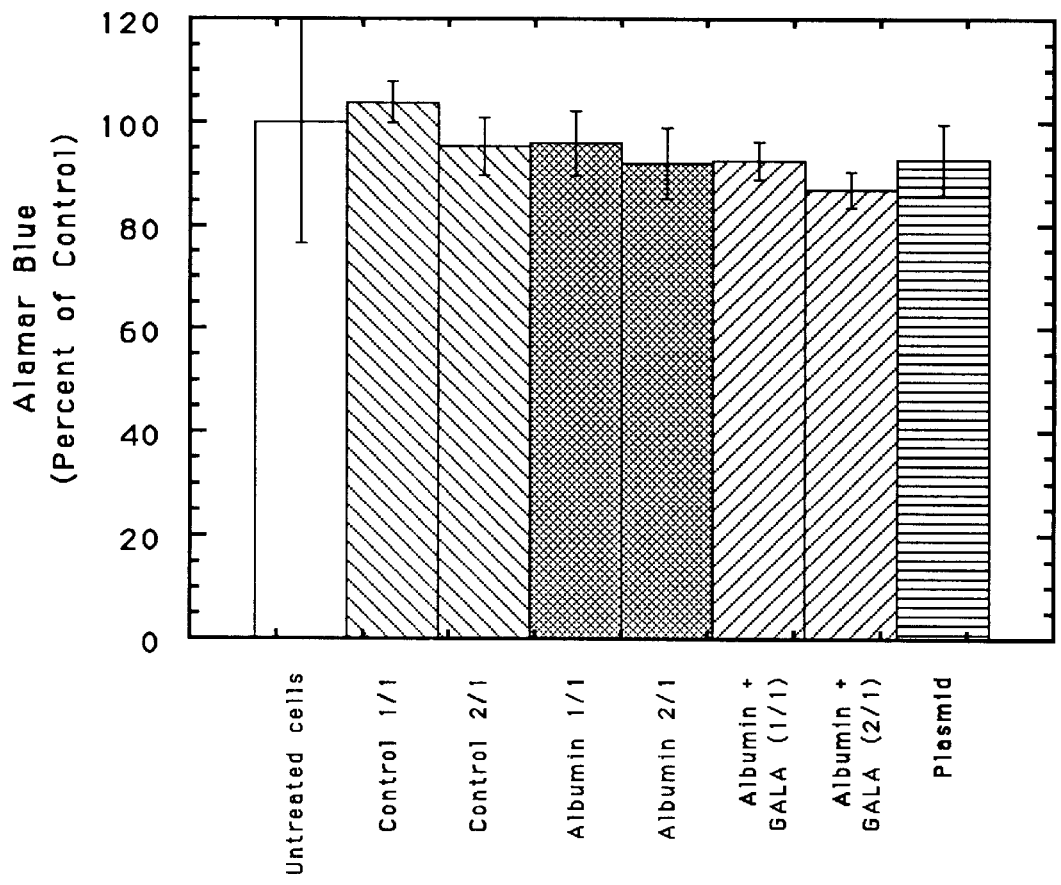
FIG. 2 shows a comparison of the effect of lipoplexes with and without HSA, and with and without GALA, on the viability of human macrophages.

THE EFFECT OF THE DIFFERENT COMPLEXES ON CELL VIABILITY. Cationic liposomes can be toxic to cells, depending on the lipid concentration, duration of treatment, the cell type and the confluency of the culture (Konopka, K. et al., *Biochim. Biophys. Acta* (1996) 1312:186–196. See also (Ciccarone, V., et al., *Focus* (1993) 15:80–83). To evaluate whether DOTAP:DOPE/DNA complexes were toxic to cells, cell viability was assessed following transfection. The colorimetric Alamar Blue assay measures the redox capacity of cells due to the production of metabolites, as a result of cell growth, and allows determination of viability over the culture period without the detachment of adherent cells. Cell viability was not affected significantly when DOTAP:DOPE/DNA complexes were incubated for 4 hours at 37° C. with human macrophages, followed by a 48 h incubation (FIG. 2). Cell metabolic activity was unaltered even for the highest lipid/DNA charge ratio tested (2/1), where about 8 μg of total lipid were used. The addition of HSA or the fusogenic peptides did not result in any toxicity to the cells. Cell viability was expressed as the percentage of the untreated control cells. Data represent the mean±standard deviation obtained from duplicate wells. These results were confirmed by both total cell protein quantification and morphological observations for treated and untreated cells (data not shown).

EVALUATION OF TRANSFECTION EFFICIENCY. To investigate whether the enhancement of transfection mediated by the association of HSA or the fusogenic peptides was due to an increase in the number of cells transfected or only due to an enhancement of gene expression, we evaluated the transfection efficiency, defined as the percentage of treated cells that express the transgene. For this purpose the plasmid pCMV.SPORT encoding β-galactosidase was associated with the complexes and cells transfected as described in Methods. The results, presented as the percentage of cells scored for the expression of β-galactosidase (blue cells) are shown in Table 1. The association of HSA or fusogenic peptides with the lipid/DNA complexes resulted in an increase in the number of cells that were detectably transfected. In the case of the 1/1 charge ratio complexes, the percentage of cells scored as expressing β-galactosidase increased from 2% for controls to 25% with HSA.

TABLE 1

EXPRESSION OF β -GAL IN HeLa CELLS (% of blue cells):
EFFECT OF THE ASSOCIATION OF HSA WITH DOTAP:DOPE/DNA
COMPLEXES OF DIFFERENT CHARGE RATIOS

| Charge ratio (lipid/DNA) | 1/2 | 1/1 | 2/1 |
|---|---|---|---|
| Control | 0% | 1–2% | 1% |
| +HSA | 5–10% | 20–25% | 5% |

The liposomes were complexed, in the presence or absence of 32 m g of HSA with 1 m g of pCMV.SPORT-β-gal at the indicated theoretical lipid/DNA charge ratios. β-gal expression was observed as described in Methods. The percentage of cells exhibiting β-gal activity was evaluated by counting 1000 cells in duplicate wells.

These results suggest that a correlation between transfection activity (level of luciferase expression) and transfection efficiency (the percentage of cells transfected) can be established in this system. It should be noted that the experiments were not designed to maximize the efficiency of transfection, but to explore the ability to use non-ligand proteins such as HSA, along with various +/−charge ratios, in transfection activity. Therefore, the efficiency of transfection shown herein may not reflect the utility or novelty of the invention.

Figure 3:
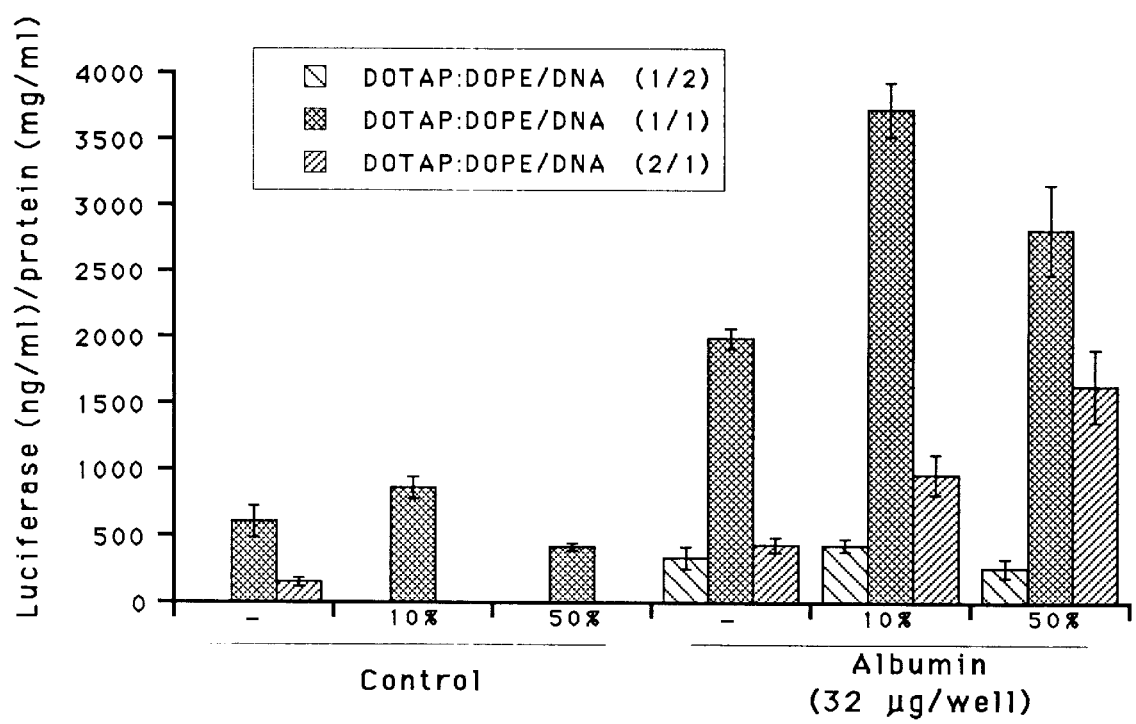
FIG. 3 shows a comparison of the effect of the presence of serum during transfection on luciferase gene expression in COS-7 cells.

EFFECT OF SERUM ON TRANSFECTION. Transfection of certain cell types by some cationic liposome compositions is sensitive to the presence of serum (Ciccarone, et al. (1993), supra; Li, S. and L. Huang, *J. Liposome Res.* (1996) 6:589–608 and Cheng (1997). The inhibition of gene delivery by serum is considered to be one of the limitations to their application in vivo (Li. S. and L. Huang, (1996), supra). Therefore, the effect of serum on the levels of transfection mediated by the above described complexes was also examined. For this purpose, complexes were added to cells in the presence of cell culture medium containing 10% or 50% FBS and incubated for 4 hours at 37° C., as described in Methods. FIG. 3 illustrates the level of transfection observed with control complexes, or HSA-associated complexes at different lipid/DNA charge ratios as shown by luciferase gene expression in COS-7 cells. Cells were covered with 0.3 ml of DME-HG enriched with 0, 10 or 50% FBS before lipid/DNA complexes were added. The liposomes were complexed, in the presence or absence of 32 μg of HSA with 1 μg of pCMVluc at the indicated theoretical lipid/DNA charge ratios. After an incubation for 4 hours, the medium was replaced with 1 ml of medium containing FBS and the cells were further incubated for 48 hours. The level of gene expression was evaluated as described in Methods. The data are expressed as ng of luciferase per mg of total cell protein. Data represent the mean±standard deviation obtained from triplicate wells.

The presence of serum did not cause a reduction of the levels of transfection for the different complexes tested. These data suggest that the complexes (either net negatively or positively charged, or neutral) remain effective despite any possible interaction with serum components. The fact that transfection mediated by the DOTAP:DOPE liposomes, with or without HSA, is not affected by the presence of serum not only results in a simplification of the transfection procedure, since the washing steps can be eliminated, but also increases the likelihood that these complexes can be utilized for gene delivery in vivo. This is a significant and totally unexpected improvement over existing technology.

COMPETITIVE INHIBITION STUDIES. To elucidate the cellular mechanisms of gene delivery by the ternary lipoplexes, an excess of free HSA (8 mg/0.3 ml of DME-HG medium) was added to COS-7 cells and incubated for 30 min at 370° C. prior to the addition of ternary complexes (cationic liposomes, pCMVluc plasmid, HSA) at an optimized charge ratio (1/1 lipid/DNA). Complexes were incubated with the cells for one hour. The medium was then replaced with DME-HG containing 10% FBS, and the cells were further incubated for 48 hours before being harvested for luciferase activity measurements. The level of gene expression was evaluated as described in Methods. The data are expressed as ng of luciferase per mg of total cell protein (mean±standard deviation obtained from triplicate wells), and are representative of 2 independent experiments.

Figure 4:
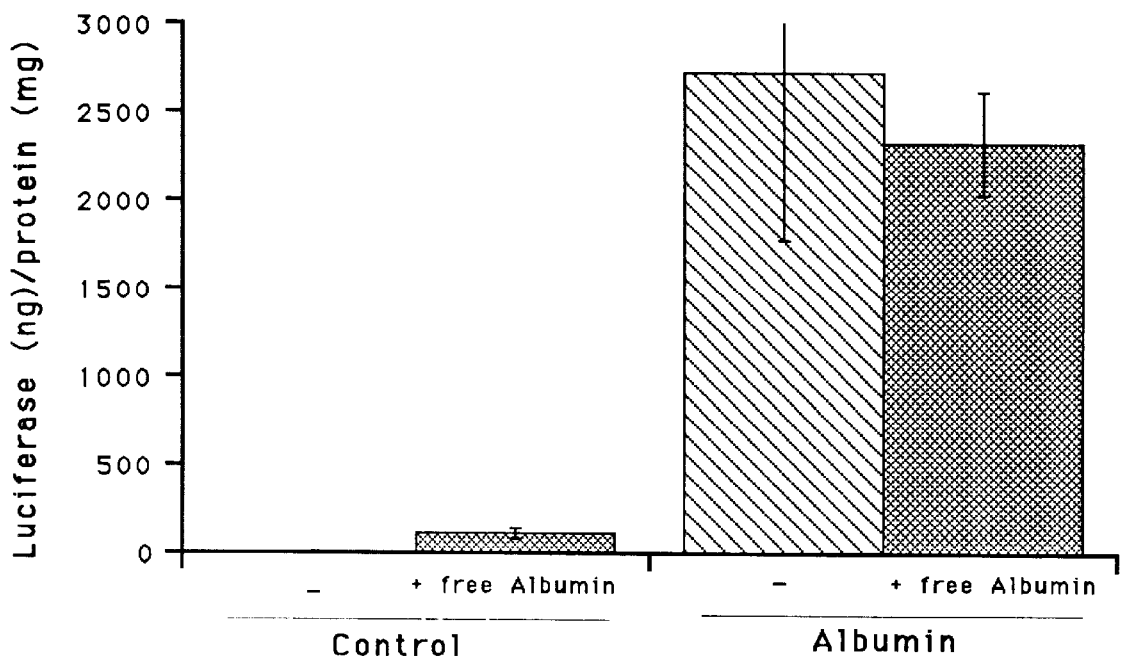
FIG. 4 shows a competitive inhibition study demonstrating the effect of the presence of excess HSA on luciferase gene expression in COS-7 cells.

Curiously, the presence of this large excess of free HSA (which represents 250 times the amount of HSA associated to the complexes) in the medium had no significant effect on the levels of transfection mediated by ternary complexes (FIG. 4). The lack of competitive inhibition illustrates the notion that HSA does not specifically bind to cell receptors nor do the ternary complexes containing HSA. Also significant is the observation that the addition of HSA after the formation of the liposome/DNA lipoplex does not enhance transfection to an appreciable extent. Therefore, the particular method and sequence of preparation of the ternary complex is essential.

EXAMPLES

Example 1
Enhancement of Transfection of COS-7 Epithelial Tumor Cells by Ternary Complexes of Cationic Liposomes-DNA-HSA.

Figure 5:
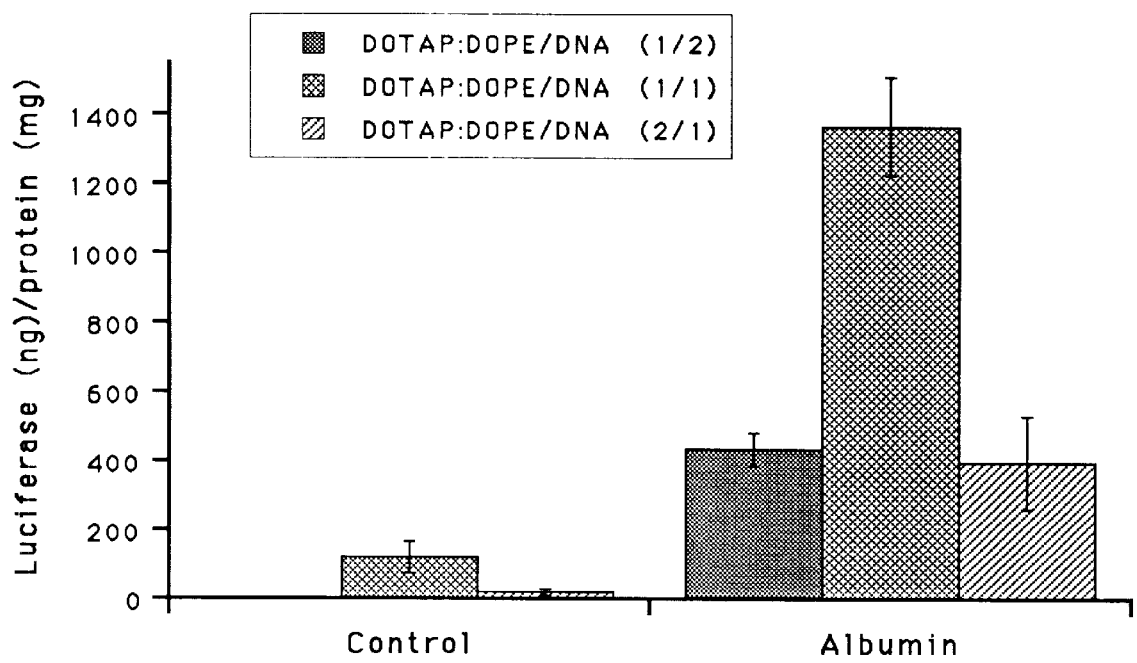
FIG. 5 shows a comparison of the effect of the presence or absence of HSA in lipoplexes on luciferase gene expression in COS-7 cells.

Since it was found that association of 32 µg of HSA resulted in the highest levels of transfection, further studies were performed under these conditions but extended to other lipid/DNA charge ratios and other cell lines. FIG. 5 shows the levels of transfection of COS-7 cells obtained with different lipid/DNA (+/−) charge ratios in the presence or absence of HSA as measured by luciferase gene expression. Cells were rinsed twice with serum-free medium and then covered with 0.3 ml of DME-HG before lipid/DNA complexes were added. The liposomes were complexed, in the presence or absence of 32 µg of HSA, with 1 µg of pCMVluc at the indicated theoretical lipid/DNA charge ratios. After an incubation for 4 hours, the medium was replaced with DME-HG containing 10% FBS and the cells were further incubated for 48 hours. The level of gene expression was evaluated as described in Methods. The data are expressed as ng of luciferase per mg of total cell protein (mean±standard deviation obtained from triplicate wells), and are representative of 2 independent experiments.

The presence of HSA enhanced transfection for all the lipid/DNA charge ratios tested. However, it is of interest to observe that this enhancement was particularly pronounced for the negatively charged complexes. It is also interesting to note that in the presence of HSA the highest levels of transfection were obtained for the 1/1 (theoretically neutral) lipid/DNA charge ratio. This observation suggests that a net positively charged lipid/DNA complex is not required to obtain relatively high levels of transfection. In fact, when complexes with 2/1 (+/−) charge ratios were tested, luciferase expression decreased compared to that of the 1/1 complex. These results also indicate that, contrary to common thought, higher positive to negative charge ratios do not enhance gene transfer or expression mediated by HSA. A similar tendency was also observed for the plain lipid/DNA complexes. Highly positively charged complexes have been proposed to be more stable in the biological milieu, since an excess of positive charge may result in a more compact or condensed complex, enabling better protection of the DNA molecule against nucleases (Gershon, H., et al. *Biochemistry* (1993) 32:7143–7151. However, for the same reasons (i.e. more stable or compact DNA), a decrease of transfection may also occur (as obtained with the 2/1 lipid/DNA complexes) due to the difficulty of dissociation of DNA from the complex and its subsequent release into the cytoplasm.

Example 2
Enhancement of Transfection of HeLa Epithelial Tumor Cells by Ternary Complexes of Cationic Liposomes-DNA-HSA.

Figure 6:
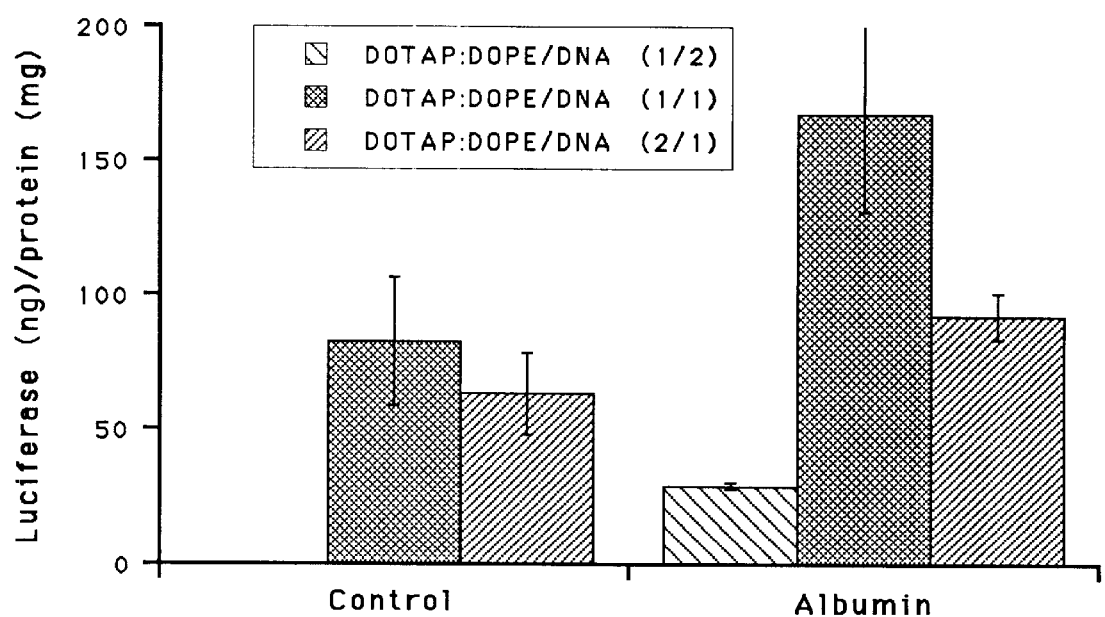
FIG. 6 shows a comparison of the effect of the presence or absence of HSA in lipoplexes on luciferase gene expression in HeLa cells.

Different cell lines exhibit largely varying levels of transfection activity with the same gene vector (Legendre J-Y and F. C. Szoka Jr. *Proc Natl Acad Sci USA* (1993) 90: 893–897: Ciccarone, V. et al, *Focus* (1993) 15: 80–83: Li, S. and L. Huang *J Liposome Res* (1996) 6:589–608. To test whether DOTAP:DOPE/DNA complexes associated with HSA were also effective in other cell lines we performed experiments with HeLa cells (FIG. 6 ) which have been used in previous transfection studies Ciccarone, 1993. Cells were rinsed twice with serum-free medium and then covered with 0.3 ml of DME-HG before lipid/DNA complexes were added. The liposomes were complexed, in the presence or absence of 32 µg of HSA, with 1 µg of pCMVluc at the indicated theoretical lipid/DNA charge ratios. After an incubation for 4 hours, the medium was replaced with DME-HG containing 10% FBS and the cells were further incubated for 48 hours. The level of gene expression was evaluated as described in Methods. The data are expressed as ng of luciferase per mg of total cell protein (mean±standard deviation obtained from triplicate wells), and are representative of 2 independent experiments. The association of HSA with the lipoplexes also resulted in a significant enhancement of the levels of luciferase expression in HeLa cells, although to a lower extent than in COS-7 cells.

Example 3
Transfection of Lymphocytes by Ternary Complexes.

Figure 7:
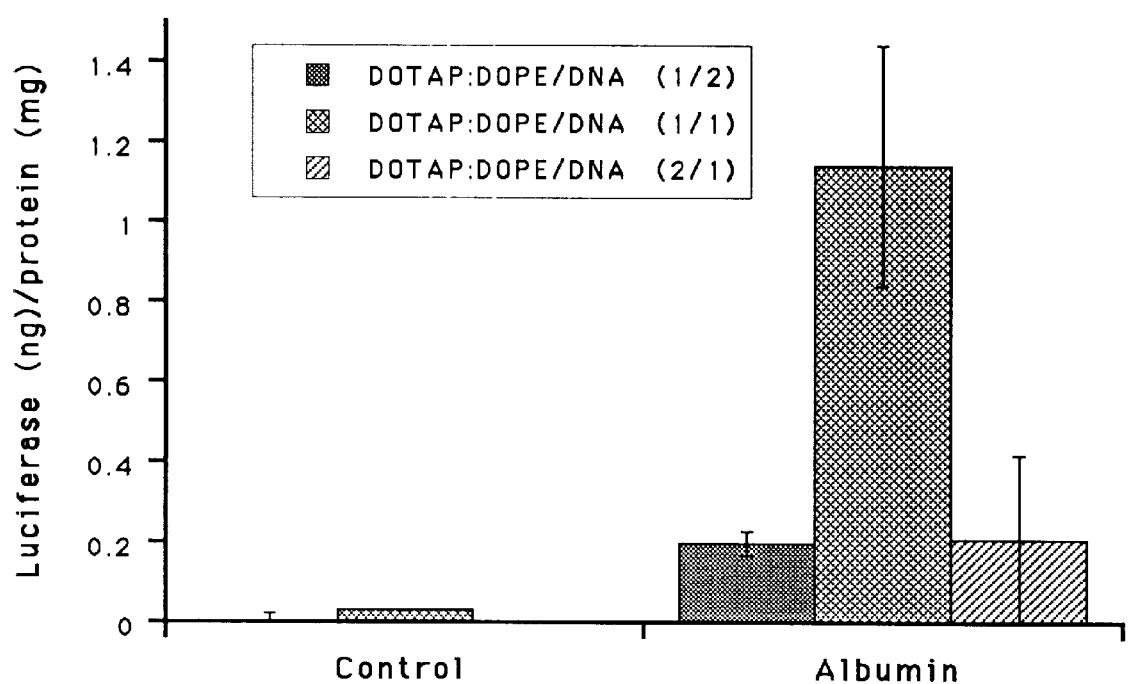
FIG. 7 shows a comparison of the effect of the presence or absence of HSA in lipoplexes on luciferase gene expression in T-lymphocytic H9 cells.

Lymphocytes play a major role in the immune system and represent an important target for gene transfer studies aimed at human gene therapy. Adoptive cellular immunotherapy based on the use of genetically modified T-cells represents a promising strategy to increase the immune response against viral infections and malignant diseases, as well as to correct single gene defects in T-cell immunodeficiency syndromes (adenosine deaminase deficiency) (Heslop, H. E., et al., *Nat. Med.* (1996) 2: 551–555: Hwu, P., et al.,*J. Immunol.* (1993) 150: 4104–4115: Blaese, R. M., et al., *Science* (1995) 270: 475–480: Hege, K. M., and M. R. Roberts, *Curr. Opin. Biotech.* (1996) 7:629–634: Tran, A-C, et al., *J. Immunol.* (1994) 155: 1000–1009. CD4-positive T-lymphocytes are one of the predominant cell reservoirs for HIV-1. "Intracellular immunization" of these cells, aiming at inhibiting viral replication, has been pursued by introduction of therapeutic genes whose expression would lead to suppression of HIV integration, to inhibition of proviral gene expression (Yu, M., et al., *Gene Ther.* (1994) 1: 13–26: Konopka K, et al., *J. Drug Targeting* (1998, in press) or to activation of suicide genes in virally infected cells (Harrison, G. S., et al., *Hum. Gene Ther.* (1992) 3: 461–469). Two lymphocyte cell lines were used to assess the ability of HSA-associated lipoplexes to transfect lymphocytes. H9 cells are a CD4+ clonal derivative of the Hut78 T-cell line, which are readily infectable by HIV (Mann, D. L., et al., *AIDS Res. Hum. Retroviruses* (1989) 5: 253–255: Lusso, P., *J. Virol.* (1995) 69: 3712–3720. T lymphocytic H9 cells were rinsed twice with serum-free medium and 106 cells/0.3 ml of medium aliquoted into polypropylene culture tubes before lipid/DNA complexes were added. The liposomes were complexed, in the presence or absence of 32 µg of HSA, with 1 µg of pCMVluc at the indicated theoretical lipid/DNA charge ratios. After an incubation for 4 hours (in 5% $CO_2$ at 37° C. cells were centrifuged (at 900 rpm for 5 min) the medium was replaced with medium containing FBS, and the cells were further incubated for 48 hours. Results are shown in FIG. 7. The data, expressed as ng of luciferase per mg of total cell protein, indicate the mean±standard deviation obtained from triplicate wells, and are representative of 2 independent experiments. HSA-lipoplexes greatly enhanced gene expression.

Example 4
Gene Transfer into B Lymphocytic TF228.1.16 Cells.

Effect of HSA complexation with DOTAP:DOPE liposomes on transfection.

Figure 8:
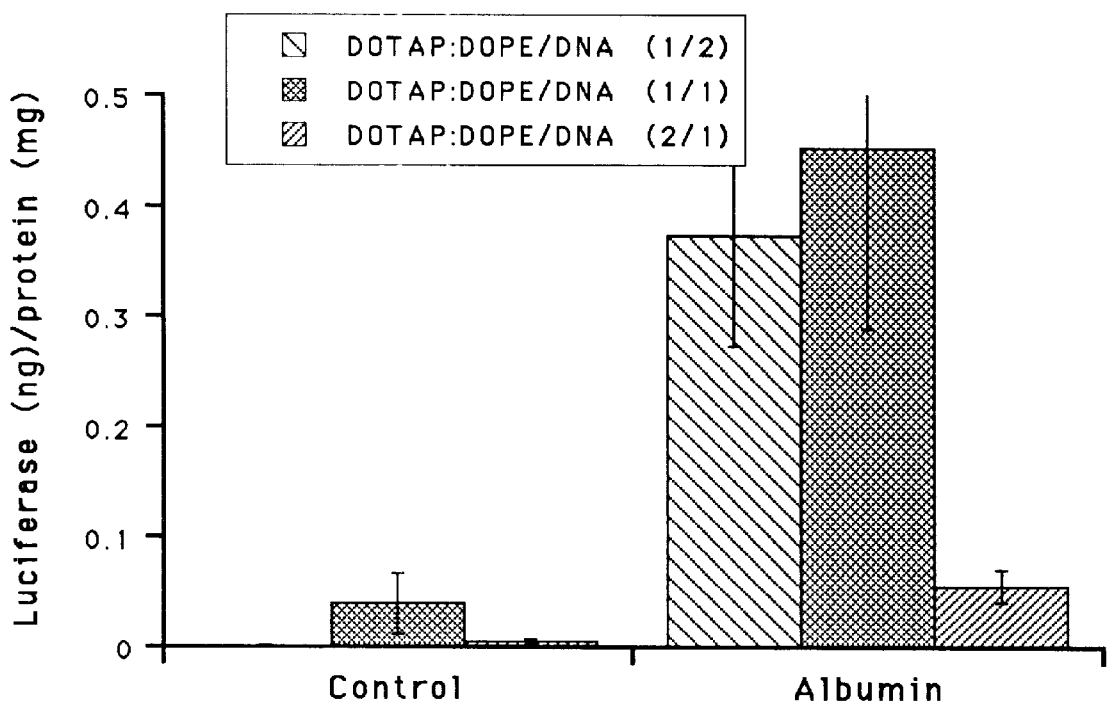
FIG. 8 shows a comparison of the effect of the presence or absence of HSA in lipoplexes on luciferase gene expression in B-lymphocytic TF228.1.16 cells.

B lymphocytic TF228.1.16 cells stably expresses functional HIV envelope proteins on the cell surface (Jonak Z L, et al., *AIDS Res Hum Retroviruses* (1993) 9: 23–32). Cells were rinsed twice with serum-free medium and $10^6$ cells/0.3 ml of medium aliquoted into polypropylene culture tubes before lipid/DNA complexes were added. The liposomes were complexed, in the presence or absence of 32 μg of HSA, with 1 μg of pCMVluc at the indicated theoretical lipid/DNA charge ratios. After an incubation for 4 hours (in 5% $CO_2$ at 37° C.) cells were centrifuged (at 900 rpm for 5 min) the medium was replaced with medium containing FBS, and the cells were further incubated for 48 hours. The data, shown in FIG. 8, are expressed as ng of luciferase per mg of total cell protein, indicate the mean±standard deviation obtained from triplicate wells, and are representative of 2 independent experiments. HSA-lipoplexes greatly enhance gene expression.

Example 5
Effect of the Association of HSA and/or Fusogenic Peptides with Cationic Liposome-DNA Complexes on Transfection of Human Blood Monocyte-derived Macrophages.

The multitude of effects of macrophages on a large variety of biological processes and pathologies render these cells crucial targets for gene therapeutic interventions (Turpin, J. A., and G. Lopez-Berestein, In: G. Lopez-Berestein and J. Klostergaard (eds.) *Mononuclear Phagocytes in Cell Biology*. CRC Press, Boca Roton (1993), p.p. 71–99: Ohashi, T., et al., *Proc Natl Acad Sci USA* (1992) 89:11332–11336: Correll PH, et al., *Blood* (1992) 80:331–336: Freas, D. L., et al., *Hum. Gene Ther.* (1993) 4: 283–290: Karlsson, S., et al., *Bone Marrow Transplant* (1993) 11 (Suppl. 1):124–127). The commonly used synthetic gene delivery vectors have not been successful in transfecting these non-dividing cells. Therefore, a combined strategy for the transfection of macrophages was designed based on the ability of cationic liposomes to condense and carry DNA, the facilitation of gene delivery by HSA, and the promotion of cytoplasmic delivery of DNA by a pH-sensitive fusogenic peptide, described by the inventors elsewhere (Simoes, S., et al. *Gene Therapy* (1998), in press). DOTAP:DOPE liposomes were mixed with 32 μg of HSA and/or 0.6 μg of a fusogenic peptide (GALA) and then mixed with 1 μg of pCMVLuc plasmid. (GALA is a 30 amino acid, pH-sensitive, amphipathic peptide whose sequence is known—Subbarao, N. K., et al., *Biochemistry* (1987) 26:2964–2972: Parente, R. A., et al., *J. Biol. Chem.* (1988) 263: 4724–4730.) Macrophages were obtained by plating monocytes in DME-HG supplemented with 20% FBS and 10% human AB serum for 7 days. hGM-CSF was added to the wells (final concentration: 100 μl/ml) at the second day of differentiation. After rinsing the cells with serum-free DME-HG medium, complexes were added and the cells incubated for 4 hours at 37° C. After removing the complexes, the cells were further incubated for 48 hours in medium containing 20% of FBS. The level of gene expression was evaluated as described in Methods. The data are expressed as ng of luciferase per mg of total cell protein (mean∓standard deviation obtained from triplicate wells), and are representative of 2 independent experiments.

Figure 9:
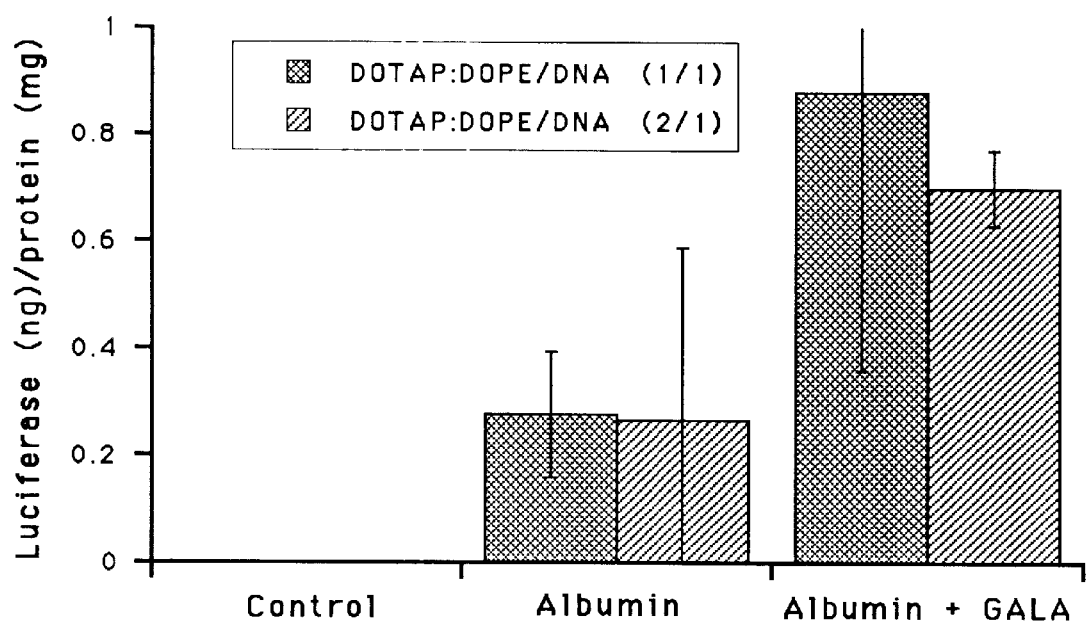
FIG. 9 shows a comparison of the effect of the presence or absence of HSA or HSA and GALA on luciferase gene expression in human blood monocyte-derived macrophages.

The use of this strategy resulted in significant gene transfer compared to conventional lipoplexes, the highest levels of transfection being observed when a 2/1 (+/−) lipid/DNA charge ratio was used (FIG. 9). The quaternary complexes of cationic liposomes, DNA, HSA and the peptide GALA presented a net negative charge. The use of net negatively charged complexes may obviate many of the in vivo limitations associated with the use of cationic synthetic vectors.

MATERIALS & METHODS

The cationic lipid 1,2-dioleoyl-3-(trimethylammonium) propane (DOTAP), and dioleoylphosphatidylethanolamine (DOPE), were purchased from Avanti Polar Lipids (Alabaster, Ala.). The pCMVluc plasmid (VR-1216) was a generous gift of Dr. P. Feigner (Vical, Inc., San Diego, Calif.). The plasmid pCMV.SPORT-β-gal and the β-gal staining kit were obtained from Gibco BRL Life Technologies (Gaithersburg, Md.) and Invitrogen Corporation (San Diego, Calif.), respectively. Alamar Blue dye was purchased from AccuMed International Companies (Westlake, Ohio). NaCl, 2-[N-morpholino]ethane-sulfonic acid (MES), and N-[2-hydroxyethyl] piperazine-N'-[2-ethanesulfonic acid] (HEPES) were obtained from Sigma (St. Louis, Mo.).

Liposome Preparation

Cationic liposomes composed of DOTAP:DOPE (1:1 weight ratio) were prepared by first drying a film of lipid under argon and then in a vacuum oven at room temperature, and hydrating the lipid film with 1 ml deionized water at a final concentration of 5 mg/ml. The multilamellar vesicles obtained were then sonicated briefly under argon, extruded 21 times through polycarbonate filters of 50 nm pore diameter using a Liposofast device (Avestin, Toronto, Canada), diluted 5 times with deionized water and filter-sterilized utilizing Millex 0.22 μm pore-diameter filters.

Cells

HeLa cells (American Type Culture Collection, Md.) were maintained at 37° C., under 5% $CO_2$, in Dulbecco's Modified Eagles's Medium-high glucose (DME-HG) (Irvine Scientific, Santa Ana, Calif.) supplemented with 10% (v/v) heat-inactivated fetal bovine serum (FBS) (Sigma, St. Louis, Mo.), penicillin (100 units/ml), streptomycin (100 μg/ml) and L-glutamine (4 mM). For transfection, $0.2 \times 10^6$ HeLa cells were seeded in 1 ml of medium in 48-well culture plates and used at 80–90% confluence. COS-7 cells (UCSF Cell Culture Facility, San Francisco, Calif.) were maintained under the same conditions described for HeLa cells. For transfection, cells were seeded in 1 ml of medium in 48-well culture plates and used at 40–60% confluence.

H9 cells (obtained from the AIDS Research and Reference Reagent Program, Division of AIDS, NIAID, NIH) were grown in RPMI 1640 medium (Irvine Scientific, Santa Ana, Calif.) supplemented with 10% (v/v) heat-inactivated fetal bovine serum (FBS) (Sigma, St. Louis, Mo.), penicillin (100 units/ml), streptomycin (100 μg/ml) and L-glutamine (2 mM). TF228.1.16 cells (a gift from Z. L. Jonak at SmithKline Beecham Pharmaceuticals, King of Prussia, Pa.) were grown in Dulbecco's Modified Eagles's Medium-high glucose (DME-HG) (Irvine Scientific, Santa Ana, Calif.) supplemented with 16% (v/v) heat-inactivated fetal bovine serum (FBS), penicillin (100 units/ml), streptomycin (100 μg/ml) and L-glutamine (4 mM). Cells were maintained at 37° C., under 5% $CO_2$, and passaged in T-25 flasks (Corning Costar, Cambridge, Mass., USA) twice weekly.

Monocytes were obtained from buffy coats by centrifugation on a Ficoll-Hypaque (Histopaque-1077: Sigma, St. Louis, Mo.) gradient and plastic adherence. Mononuclear cells separated by centrifugation were counted and plated in Dulbecco's Modified Eagle's Medium, High Glucose (DME-HG) medium without serum at a density of $1.4 \times 10^6$ cells/ml per well in 48-well plates. It was assumed that approximately 5–10% of the cells plated were recovered as macrophages. The cells were allowed to adhere overnight, then washed and the medium was replaced with DME-HG supplemented with 20% (v/v) heat-inactivated fetal bovine serum (FBS, Sigma, St Louis, Mo.), 10% (v/v) human AB serum (Advanced Biotechnologies, Columbia, Md.), penicillin (100 U/ml), streptomycin (100 μg/ml) and L-glutamine (2 mM). The cells were left undisturbed in this medium for 6–7 days for differentiation to occur. In some experiments human granulocyte-macrophage colony stimulating factor (hGM-CSF) (Boehringer Mannheim Biochemica, Indianopolis, Ind.) was added to the wells (final concentration of 100 µl/well) at the second day of differentiation. In other experiments, cells were cultured for 8 more days in medium containing 20% FBS, antibiotics and L-glutamine, but in the absence of hGM-CSF.

Preparation of the Ternary Complexes

Complexes were prepared by sequentially mixing 100 µl of a solution of 100 mM NaCl, 20 mM Hepes, pH 7.4, with or without 32 µg iron-saturated human serum albumin with 2.5, 5, or 10µl liposomes and incubated at room temperature for 15 min. One hundred µl of buffer containing 1 µg of pCMVluc or 1 µg pCMV.SPORT-β-gal plasmid was then added and gently mixed, and the mixture was further incubated for 15 min at room temperature. Peptide complexes were prepared in a similar manner, with varying amounts of peptide, as indicated in the figures.

Transfection Activity

Cells were rinsed twice with serum-free medium and then covered with 0.3 ml of DME-HG before lipid/DNA complexes were added. Lipid/DNA complexes were added gently to cells in a volume of 0.2 ml per well. After an incubation for 4 hours (37° C., under 5% $CO_2$) the medium was replaced with DME-HG containing 10% FBS, and the cells were further incubated for 48 hours. The cells were then washed twice with phosphate-buffered saline (PBS) and 100 µl of lysis buffer (Promega, Madison, Wis.) were added to each well. The level of gene expression in the lysates was evaluated by measuring light production by luciferase using a scintillation counter protocol (Promega). The protein content of the lysates was measured by the Dc Protein Assay reagent (Bio-Rad, Hercules, Calif.) using bovine serum albumin as the standard. The data were expressed as ng of luciferase (based on a standard curve for luciferase activity) per mg of total cell protein.

Transfection Efficiency

Transfection efficiency was evaluated by scoring the percentage of cells expressing β-galactosidase. Briefly, cells transfected with 1 µg of pCMV.SPORT-β-gal were washed with PBS, fixed in a solution of 2% formaldehyde and 0.2% glutaraldehyde, and stained with an X-gal containing solution. The cells were incubated at 37° C. for 24 hours and then examined under a phase contrast microscope for the development of blue color. The percentage of cells exhibiting β-gal activity was evaluated by counting 1000 cells in duplicate wells.

Cell Viability Assay

Cell viability following transfection under the different experimental conditions was quantified by a modified Alamar Blue Assay. Briefly, 1 ml of 10% (v/v) Alamar Blue dye in complete DME medium was added to each well 45 hours following transfection. After 2.5 to 4 hours of incubation at 37° C., 200 µl of the supernatant were collected from each well and transferred to 96-well plates. The absorbance at 570 nm and 600 nm was measured with a microplate reader (Molecular Devices, Menlo Park, Calif.). Cell viability (as a percentage of control cells) was calculated according to the formula ($A_{570}$–$A_{600}$) of treated cells× 100/($A_{570}$–$A_{600}$) of control cells.

In the foregoing, the present invention has been described with reference to suitable embodiments, but these embodiments are only for purposes of understanding the invention and various alterations or modifications are possible so long as the present invention does not deviate from the claims that follow.

What is claimed is:

1. A method for intracellular delivery of a biologically active agent to a target cell comprising:
   a) combining a non-receptor-binding polypeptide and a cationic lipid to form a first mixture such that said polypeptide and lipid become associated;
   b) adding to said first mixture said biologically active agent to form a second negatively charged complex mixture such that said agent becomes associated with said lipid; and,
   c) introducing said second mixture to said cell.

2. The method of claim 1 further comprising the step of incubating said first mixture prior to addition of said biologically active agent.

3. The method of claim 1 further comprising the step of incubating said second mixture prior to introduction of said second mixture to said cell.

4. The method of claim 1 wherein said cationic lipid is combined with a neutral lipid, forming a cationic liposome formulation thereby.

5. The method of claim 4 wherein said neutral lipid is selected from the group consisting of dioleoylphosphatidylethanolamine, and cholesterol.

6. The method of claim 4 wherein said cationic liposome is a formulation of 1,2-dioleoyl-3-(trimethylammonium) propane and dioleoylphosphatidylethanolamine.

7. The method of claim 1 wherein said cationic lipid is selected from the group consisting of DOTMA, DDAB, DOSPA, DORI, DORI-ester, DORI-ether, DMRIE, DOTAP, and TM-TPS.

8. The method of claim 1 wherein the seqence of the non-receptor binding polypeptide is substantially similar to the sequence of albumin.

9. The method of claim 1 wherein the non-receptor-binding polypeptide is a protein.

10. The method of claim 9 wherein said non-receptor-binding protein is selected from the group consisting of human serum albumin, bovine serum albumin, porcine serum albumin, murine serum albumin, and apotransferrin.

11. The method of claim 9 wherein said non-receptor protein is human serum albumin.

12. The method of claim 1 wherein said biologically active agent is selected from the group consisting of a polydeoxyribonucleotide, a polyribonucleotide, and a polypeptide.

13. The method of claim 10 wherein said biologically active agent comprises a polydeoxyribonucleotide.

14. The method of claim 13 wherein the charge ratio of cationic liposome formulation to polydeoxyribonucleotide is between 2:1 and 1:2.

15. The method of claim 13 wherein said charge ratio of cationic liposome formulation to polydeoxyribonucleotide is 1 to 1.

16. The method of claim 13 wherein said polydeoxyribonucelotide encodes a gene product.

17. The method of claim 12 wherein said biologically active agent comprises a polyribonucleotide.

18. The method of claim 12 wherein said biologically active agent comprises a protein.

19. The method of claim 1 wherein said biologically active agent is a drug.

20. The method of claim 1 wherein said cell is in culture.

21. The method of claim 20 wherein said culture is a primary culture.

22. The method of claim 20 wherein said cell is a human cell.

23. The method of claim 1 wherein said cell is in vivo.

24. The method of claim 23 wherein said cell is a human cell.

25. The method of claim 1 wherein said second mixture is introduced to said cell in the presence of serum.

26. The method of claim 25 where the concentration of said serum is at least 10%.

27. The method of claim 1 additionally comprising incubating the first mixture with a fusogenic peptide prior to the addition of said biologically active agent.

28. The method of claim 27 wherein said fusogenic peptide is selected from the group consisting of GALA, and HA-2.

29. A carrier composition for intracellular delivery of a biologically active agent to a target cell comprising a negatively charged complex mixture of a cationic lipid and a non-receptor-binding polypeptide.

30. The composition of claim 29 wherein said cationic lipid is first combined with a neutral lipid forming a cationic liposome thereby.

31. The composition of claim 29 wherein said non-receptor-binding polypeptide is a protein selected from the group consisting of: human serum albumin, bovine serum albumin, porcine serum albumin, murine serum albumin, and apotransferrin.

32. The composition of claim 29 wherein said cationic lipid is selected from a group consisting of DOTMA, DDAB, DOSPA, DORI, DORI-ester, DORI-ether, DMRIE, DOTAP, and TM-TPS.

33. The composition of claim 29 wherein said neutral lipid is selected from the group consisting of dioleoylphosphatidylethanolamine, and cholesterol.

34. The composition of claim 29 further comprising a biologically active agent.

35. The composition of claim 34 wherein said biologically active agent is selected from the group consisting of: a polydeoxyribonucleotide, a polyribonucleotide, a polypeptide, and a drug.

36. The composition of claim 34 wherein said biologically active agent is a a polydeoxyribonucleotide that encodes a gene.

37. The composition of claim 34 wherein said biologically active agent is a polypeptide.

38. A method of transfecting a cell with a polynucleotide sequence comprising:

a) combining a non-receptor-binding polypeptide and a cationic lipid to form a first mixture such that said polypeptide and lipid become associated;

b) adding to said first mixture said polynucleotide sequence to form a second negatively chared complex mixture such that said polynucleotide becomes associated with said lipid; and, c) introducing said second mixture to said cell.

39. The transfection method of claim 38 where said polynucleotide sequence comprises a gene.

40. The transfection method of claim 38 where said non-receptor-binding polypeptide is serum albumin.

41. The transfection method of claim 38 where said cationic lipid is combined with a neutral lipid forming a cationic liposome thereby.

* * * * *